US008900594B2

(12) United States Patent
Zou et al.

(10) Patent No.: US 8,900,594 B2
(45) Date of Patent: Dec. 2, 2014

(54) **ORAL RECOMBINANT *HELICOBACTER PYLORI* VACCINE AND PREPARING METHOD THEREOF**

(75) Inventors: Quanming Zou, Chongqing (CN); Wende Tong, Chongqing (KR); Xuhu Mao, Chongqing (KR); Gang Guo, Chongqing (KR); Dongshui Lu, Chongqing (KR); Chao Wu, Chongqing (KR); Hao Zeng, Chongqing (KR); Yichao Wang, Chongqing (KR); Jun Yang, Chongqing (KR); Weijun Zhang, Chongqing (KR); Kaiyun Liu, Chongqing (KR); Ping Luo, Chongqing (KR)

(73) Assignee: Wuhu Kangwei Biotechnology Co., Ltd (CN)

( * ) Notice: Subject to any disclaimer, the term of this patent is extended or adjusted under 35 U.S.C. 154(b) by 1424 days.

(21) Appl. No.: 12/310,658

(22) PCT Filed: Sep. 5, 2007

(86) PCT No.: PCT/CN2007/002655
§ 371 (c)(1),
(2), (4) Date: Nov. 4, 2009

(87) PCT Pub. No.: WO2008/040155
PCT Pub. Date: Apr. 10, 2008

(65) Prior Publication Data
US 2011/0171315 A1    Jul. 14, 2011

(30) Foreign Application Priority Data
Sep. 5, 2006   (CN) .......................... 2006 1 0095094

(51) Int. Cl.
| | | |
|---|---|---|
| *A61K 39/116* | (2006.01) | |
| *A61K 9/50* | (2006.01) | |
| *A61K 39/00* | (2006.01) | |
| *A61K 39/385* | (2006.01) | |
| *C12N 9/96* | (2006.01) | |
| *C12N 15/00* | (2006.01) | |
| *C07H 21/04* | (2006.01) | |
| *A61K 47/26* | (2006.01) | |
| *A61K 39/02* | (2006.01) | |
| *C12N 9/80* | (2006.01) | |
| *C07K 14/205* | (2006.01) | |
| *A61K 9/19* | (2006.01) | |
| *C07K 14/245* | (2006.01) | |

(52) U.S. Cl.
CPC . *C12N 9/80* (2013.01); *A61K 47/26* (2013.01); *A61K 39/00* (2013.01); *C07K 2319/55* (2013.01); *A61K 39/105* (2013.01); *C07K 14/205* (2013.01); *A61K 9/19* (2013.01); *C07K 2319/00* (2013.01); *C07K 14/245* (2013.01); *A61K 2039/55544* (2013.01); *A61K 2039/542* (2013.01)

USPC ................. 424/203.1; 424/499; 424/192.1; 424/193.1; 424/197.11; 435/188; 435/320.1; 536/23.2

(58) Field of Classification Search
CPC ............ A61K 2039/55544; A61K 2039/6037; A61K 39/39; A61K 45/06
See application file for complete search history.

(56) References Cited

U.S. PATENT DOCUMENTS

| | | | |
|---|---|---|---|
| 5,837,240 A | * | 11/1998 | Lee et al. ..................... 424/94.6 |
| 6,576,244 B1 | | 6/2003 | Weltzin et al. |
| 2006/0141021 A1 | * | 6/2006 | Wang et al. ................... 424/450 |
| 2006/0228422 A1 | * | 10/2006 | Sava et al. ..................... 424/490 |

FOREIGN PATENT DOCUMENTS

WO    WO 2007/114878    *    1/2006

OTHER PUBLICATIONS

Yuan, Chinese Journal of Biologicals, 2003; 16(4): 201-204; abstract only.*
Michetti et al., Gastroenterology, 1999; 116(4): 804-12 (abstract only).*
Gupta et al. Dev. Biol. Stand, 1998; 92: 63-78 (Abstract only).*
Tang et al., Pharmaceutical Research, 2004; 21(2): 191-191-200.*
Yuan, Xiaopeng et al: 'Expression and biological activity of fusion protein of *Helicobacter pylori* urease B subunit and *E. coli* heat-labile enterotoxin B subunit', Chin J Biologicals, 2003, 16(4), pp. 201-204, abstract only.
Chung-Dar Yang: 'Analysis of the protective capacity of SAG1 and SAG2 subunit vaccines in Balb/c mice', Doctoral dissertation of Taiwan Zhongshan University, 2004. see pp. 171-172, abstract only.
Wang, Yichao et al: 'Preparation and character of microspheres of *Helicobacter pylori* whole cell protein encapsulated by chitosan-alginate', West China Journal of Pharmaceutical Sciences, 2005, 20(5), 375-377, only abstract, sect. 1.2.1, 1.2.2, 1.3.3.
Michetti et al., 'Oral Immunization with *Helocobacter pylori* Urease B Subunit as a Treatment Against *Helicobacter* Infection in Mice', Gastroenterol, 1995, 109:115-121.
Lycke N, et al., 'Strong adjuvant properties of cholera toxin on gut mucosal immune responses to orally presented antigens', Immunology, 1986, 59(2):301-308.
Clements JD, et al., 'Adjuvant activity of *Escherichia coli* heat-labile enterotoxin and effect on the induction of oral tolerance in mice to unrelated protein antigens', Vaccine 1988, 6(3):269-277.

(Continued)

*Primary Examiner* — Gary Nickol
*Assistant Examiner* — Lakia Tongue
(74) *Attorney, Agent, or Firm* — Edwards Wildman Palmer LLP; Jeffrey D. Hsi; Gabriel J. McCool

(57) ABSTRACT

The invention relates to a recombinant protein used for immunoprophylaxis of human *Helicobacter pylori* infection and a degradable slow-releasing microsphere-encapsulated oral vaccine preparation prepared from the same, and the preparation method thereof. Said recombinant protein is composed of A2 subunit and B subunit of the LT of enterotoxigenic *Escherichia coli* and urease B subunit. The vaccine provided in the invention used in human *Helicobacter pylori* infection is safe and effective and convenient for oral intake.

10 Claims, 3 Drawing Sheets

(56) References Cited

OTHER PUBLICATIONS

Giuliani MM, et al., 'Mucosal Adjuvanticity and Immunogenicity of LTR72, a Novel Mutant of *Escherichia coli* Heat-labile Enterotoxin with Partial Knockout of ADP-ribosyltransferase Activity', J. Exp. Med., 1998, 187(7):1123-1132.

Yamamoto M, et al., 'Direct Effects on Antigen-Presenting Cells and T Lymphocytes Explain the Adjuvanticity of a Nontoxic Cholera Toxin Mutant', J. Immunol., 1999, 162:7015-7021.

Martin M, et al., 'Role of B7 Costimulatory Molecules in the Adjuvant Activity of the Heat-Labile Enterotoxin of *Escherichia coli*', J.Immunol., 2002, 169(4):1744-1752.

Tamura SI, et al., 'Effects of cholera toxin adjuvant on IgE antibody response to orally or nasally administered ovalbumin', Vaccine, 1994, 12:1238-1240.

de Hann L, et al., 'Mucosal immunogenicity of the *Escherichia coli* heat-labile enterotoxin: role of the A subunit', Vaccine, 1996;(4):260-266, 14(4).

de Haan L, et al., 'Mutants of the *Escherichia coli* Heat-Labile Enterotoxin with Reduced ADP-Ribosylation Activity or No Activity Retain the Immunogenic Properties of the Native Holotoxin', Infect Immun, Dec. 1996, vol. 64, No. 12, p. 5413-5416.

Wu Chao et al: 'Research on fusion and expression of *Helicobacter pylori* UreB and *Escherichia coli* LTB genes', Chin J Microbiol Immunol, 2002, 22(2), pp. 175-179, abstract.

International Search Report Re: PCT/CN2007/002655 dated Dec. 13, 2007.

* cited by examiner

SEQUENCE LISTING

<160> NUMBER OF SEQ ID NOS: 6

<210> SEQ ID NO 1
<211> LENGTH: 2187
<212> TYPE: DNA
<213> ORGANISM: Artificial Sequence
<220> FEATURE:
<223> OTHER INFORMATION: Description of Artificial Sequence: Synthetic
      fusion gene ltA2b-ureB sequence

<400> SEQUENCE: 1
atggctcccc agtctattac agaactatgt tcggaatatc gcaacacaca aatatatacg    60

```
ataaatgaca agatactatc atatacggaa tcgatggcag gtaaaagaga aatggttatc      120
attacattta agagcggcgc aacatttcag gtcgaagtcc cgggcagtca acatatagac      180
tcccaaaaaa aagccattga aaggatgaag gacacattaa gaatcacata tctgaccgag      240
accaaaattg ataaattatg tgtatggaat aataaaaccc ccaattcaat tgcggcaatc      300
agtatggaaa acacaattac aggtgatact tgtaatgagg agacccagaa tctgagcaca      360
atatatctca ggaaatatca atcaaaagtt aagaggcaga tattttcaga ctatcagtca      420
gaggttgaca tatataacag aattcgggat gaattatacc ctcaggatcc gatatcaatg      480
aaaaagatta gcagaaaaga atatgtttct atgtatggcc ctactacagg cgataaagtg      540
agattgggcg atacagattt gatcgctgaa gtagaacatg actacaccat ttatggcgaa      600
gagctaaaat tggtggcgg taaaacttta agagaaggca tgagccaatc cagcaacccc      660
agcaaagaag aactggattt aatcatcact aacgctttaa tcgtggatta caccggtatt      720
tataaagcgg atattggtat taagatggca aaaatcgctg gcattggcaa aggcggtaac      780
aaagacatgc aagatggcgt taaaaacaat cttagcgtgg gtcctgctac tgaagcctta      840
gctggtgaag gtttgatcgt aactgctggc ggtattgaca cacacatcca cttcatctcc      900
ccccaacaaa tccctacagc ttttgcaagc ggtgtaacaa ctatgattgg tggcggaact      960
ggccctgctg atggcactaa cgcaaccact atcactccag gcagaagaaa tttaaaatgg     1020
atgctcagag cggctgaaga atattctatg aacttaggtt tcttagctaa aggtaacact     1080
tctaacgatg cgagcttagc cgatcaaatt gaagccggtg cgattggttt taaaatccac     1140
gaagactggg gaacaactcc ttctgcaatc aaccatgcgt tagatgttgc ggacaaatac     1200
gatgtgcaag tcgctatcca cacagacact ttgaatgaag ccggttgtgt agaagacact     1260
atggcagcca ttgccgggcg cactatgcac actttccaca ctgaaggtgc tggtggtgga     1320
cacgctcctg atattattaa agtggccggc gaacacaaca ttctgcccgc ttccactaac     1380
cccactatcc ctttcaccgt gaatacagaa gcagaacaca tggacatgct tatggtgtgc     1440
caccacttgg ataaaagcat taagaagat gttcagttcg ctgattcaag gatccgccct     1500
caaaccattg cggctgaaga cactttgcat gacatgggga ttttctcaat caccagttct     1560
gactctcaag ctatgggtcg tgtgggtgaa gttatcacca gaacttggca aacagctgac     1620
aaaaacaaaa aagaatttgg ccgcttgaaa gaagaaaaag gcgataacga caacttcagg     1680
atcaaacgct acttgtctaa atacaccatt aacccagcga tcgctcatgg gattagcgag     1740
tatgtaggtt ctgtagaagt gggcaaagtg gctgacttgg tattgtggag tcccgcattc     1800
tttggcgtga aacccaacat gatcatcaaa ggcgggttca ttgcattaag tcaaatgggc     1860
gatgcgaacg cttctatccc taccccacaa ccggtttatt acagagaaat gttcgctcat     1920
catggtaaag ccaaatacga tgcaaacatc acttttgtat cccaagcggc ttatgacaaa     1980
ggcattaaag aagaattagg gcttgaaaga caagtgttgc cggtaaaaaa ttgcagaaac     2040
atcactaaaa aagacatgca attcaacgac actaccgctc acattgaagt caatcctgaa     2100
acttaccatg tgttcgtgga tgcaaagaa gtaacttcta aaccagccac taaagtgagc     2160
ttggcacaac tctttagcat tttctag                                         2187
```

<210> SEQ ID NO 2
<211> LENGTH: 728
<212> TYPE: PRT
<213> ORGANISM: Artificial Sequence
<220> FEATURE:

<223> OTHER INFORMATION: Description of Artificial Sequence: Synthetic
fusion protein ltA2b-ureB sequence

<400> SEQUENCE: 2

```
Met Ala Pro Gln Ser Ile Thr Glu Leu Cys Ser Glu Tyr Arg Asn Thr
1               5                   10                  15

Gln Ile Tyr Thr Ile Asn Asp Lys Ile Leu Ser Tyr Thr Glu Ser Met
            20                  25                  30

Ala Gly Lys Arg Glu Met Val Ile Ile Thr Phe Lys Ser Gly Ala Thr
        35                  40                  45

Phe Gln Val Glu Val Pro Gly Ser Gln His Ile Asp Ser Gln Lys Lys
    50                  55                  60

Ala Ile Glu Arg Met Lys Asp Thr Leu Arg Ile Thr Tyr Leu Thr Glu
65                  70                  75                  80

Thr Lys Ile Asp Lys Leu Cys Val Trp Asn Asn Lys Thr Pro Asn Ser
                85                  90                  95

Ile Ala Ala Ile Ser Met Glu Asn Thr Ile Thr Gly Asp Thr Cys Asn
            100                 105                 110

Glu Glu Thr Gln Asn Leu Ser Thr Ile Tyr Leu Arg Lys Tyr Gln Ser
        115                 120                 125

Lys Val Lys Arg Gln Ile Phe Ser Asp Tyr Gln Ser Glu Val Asp Ile
    130                 135                 140

Tyr Asn Arg Ile Arg Asp Glu Leu Tyr Pro Gln Asp Pro Ile Ser Met
145                 150                 155                 160

Lys Lys Ile Ser Arg Lys Glu Tyr Val Ser Met Tyr Gly Pro Thr Thr
                165                 170                 175

Gly Asp Lys Val Arg Leu Gly Asp Thr Asp Leu Ile Ala Glu Val Glu
            180                 185                 190

His Asp Tyr Thr Ile Tyr Gly Glu Glu Leu Lys Phe Gly Gly Gly Lys
        195                 200                 205

Thr Leu Arg Glu Gly Met Ser Gln Ser Ser Asn Pro Ser Lys Glu Glu
    210                 215                 220

Leu Asp Leu Ile Ile Thr Asn Ala Leu Ile Val Asp Tyr Thr Gly Ile
225                 230                 235                 240

Tyr Lys Ala Asp Ile Gly Ile Lys Asp Gly Lys Ile Ala Gly Ile Gly
                245                 250                 255

Lys Gly Gly Asn Lys Asp Met Gln Asp Gly Val Lys Asn Asn Leu Ser
            260                 265                 270

Val Gly Pro Ala Thr Glu Ala Leu Ala Gly Glu Gly Leu Ile Val Thr
        275                 280                 285

Ala Gly Gly Ile Asp Thr His Ile His Phe Ile Ser Pro Gln Gln Ile
    290                 295                 300

Pro Thr Ala Phe Ala Ser Gly Val Thr Thr Met Ile Gly Gly Gly Thr
305                 310                 315                 320

Gly Pro Ala Asp Gly Thr Asn Ala Thr Thr Ile Thr Pro Gly Arg Arg
                325                 330                 335

Asn Leu Lys Trp Met Leu Arg Ala Ala Glu Glu Tyr Ser Met Asn Leu
            340                 345                 350

Gly Phe Leu Ala Lys Gly Asn Thr Ser Asn Asp Ala Ser Leu Ala Asp
        355                 360                 365

Gln Ile Glu Ala Gly Ala Ile Gly Phe Lys Ile His Glu Asp Trp Gly
    370                 375                 380

Thr Thr Pro Ser Ala Ile Asn His Ala Leu Asp Val Ala Asp Lys Tyr
385                 390                 395                 400
```

Asp Val Gln Val Ala Ile His Thr Asp Thr Leu Asn Glu Ala Gly Cys
            405                 410                 415

Val Glu Asp Thr Met Ala Ala Ile Ala Gly Arg Thr Met His Thr Phe
            420                 425                 430

His Thr Glu Gly Ala Gly Gly His Ala Pro Asp Ile Ile Lys Val
            435                 440                 445

Ala Gly Glu His Asn Ile Leu Pro Ala Ser Thr Asn Pro Thr Ile Pro
            450                 455                 460

Phe Thr Val Asn Thr Glu Ala Glu His Met Asp Met Leu Met Val Cys
465                 470                 475                 480

His His Leu Asp Lys Ser Ile Lys Glu Asp Val Gln Phe Ala Asp Ser
            485                 490                 495

Arg Ile Arg Pro Gln Thr Ile Ala Ala Glu Asp Thr Leu His Asp Met
            500                 505                 510

Gly Ile Phe Ser Ile Thr Ser Ser Asp Ser Gln Ala Met Gly Arg Val
            515                 520                 525

Gly Glu Val Ile Thr Arg Thr Trp Gln Thr Ala Asp Lys Asn Lys Lys
            530                 535                 540

Glu Phe Gly Arg Leu Lys Glu Glu Lys Gly Asp Asn Asp Asn Phe Arg
545                 550                 555                 560

Ile Lys Arg Tyr Leu Ser Lys Tyr Thr Ile Asn Pro Ala Ile Ala His
            565                 570                 575

Gly Ile Ser Glu Tyr Val Gly Ser Val Glu Val Gly Lys Val Ala Asp
            580                 585                 590

Leu Val Leu Trp Ser Pro Ala Phe Phe Gly Val Lys Pro Asn Met Ile
            595                 600                 605

Ile Lys Gly Gly Phe Ile Ala Leu Ser Gln Met Gly Asp Ala Asn Ala
            610                 615                 620

Ser Ile Pro Thr Pro Gln Pro Val Tyr Tyr Arg Glu Met Phe Ala His
625                 630                 635                 640

His Gly Lys Ala Lys Tyr Asp Ala Asn Ile Thr Phe Val Ser Gln Ala
            645                 650                 655

Ala Tyr Asp Lys Gly Ile Lys Glu Glu Leu Gly Leu Glu Arg Gln Val
            660                 665                 670

Leu Pro Val Lys Asn Cys Arg Asn Ile Thr Lys Lys Asp Met Gln Phe
            675                 680                 685

Asn Asp Thr Thr Ala His Ile Glu Val Asn Pro Glu Thr Tyr His Val
            690                 695                 700

Phe Val Asp Gly Lys Glu Val Thr Ser Lys Pro Ala Thr Lys Val Ser
705                 710                 715                 720

Leu Ala Gln Leu Phe Ser Ile Phe
            725

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
catatggctc ctcagtctat tacagaacta tgttc                              35

<210> SEQ ID NO 4

-continued

```
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgatatcgga tcctgagggt ataattcatc ccgaattctg                         40

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taccctcagg atccgatatc aatgaaaaag attagcag                           38

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
catatgctag aaaatgctaa agagttgtgc caagc                              35
```

ORAL RECOMBINANT *HELICOBACTER PYLORI* VACCINE AND PREPARING METHOD THEREOF

CROSS-REFERENCE TO RELATED APPLICATIONS

This application is the National Stage of PCT/CN2007/002655, filed Sep. 5, 2007, which claims benefit of Chinese Application 200610095094.0, filed Sep. 5, 2006. The entire contents of each of these applications is incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 14, 2013, is named 83630(305178)_SL.txt and is 10,885 bytes in size.

TECHNICAL FIELD

The invention relates to the field of biopharmaceuticals, especially relates to a recombinant protein used for immunoprophylaxis of human *Helicobacter pylori* infection and a degradable microsphere-encapsulated slow-releasing oral vaccine preparation prepared from the recombinant protein, and preparation method thereof.

BACKGROUND OF THE INVENTION

The 2005 Nobel Prize in medicine/physiology was awarded to the two scientists who discovered the *Helicobacter pylori* (Hp). *Helicobacter pylori* is which is believed to be an important pathogenic bacterium for diseases of upper digestive tract in human and the main pathogenic cause of chronic gastritis, gastric ulcer, and duodenal ulcer. *Helicobacter pylori* World health organization (WHO) has also confirmed that Hp is a pathogenic bacterium closely related to gastric cancer, classifying it as the primary carcinogenic factor. Hp is one of the bacteria with the highest infection rate in the world, with an infection rate reaching 50% in the global population and even higher in developing countries. In China, there are as many as six hundred million people infected with Hp, and every year two hundred thousand people die of gastric cancer. Thus, Hp is a major threat to human health. Despite of positive clinical significance, today's antibiotic therapy of Hp infection still has some obvious drawbacks: 1) toxic and adverse side effects; 2) generation of drug resistant strains; 3) high cost; 4) lengthy treatment cycle and poor patient compliance; and 5) unstable therapeutic effect. On the other hand, vaccine is considered the most cost-effective means to control infectious diseases. Through inducing a specific immune response in the body, vaccination can be used to prevent or treat Hp infection. While the research progress in whole-cell vaccines is limited by the difficulty in large-scale cultivation of Hp and the existence of potential carcinogen in crude antigen, the development in genetically engineered vaccines has become the main direction owing to its safety, effectiveness, low cost, and ease in promotion and use. Although intensively researched both domestically and abroad, Hp vaccines have yet to be successful.

Urease, a nickel-dependent enzyme, catalyzes hydrolysis of urea into ammonia and carbonic acid, and is the mostly abundant protein expressed in *Helicobacter pylori* both inside cells and on cell membrane, accounting for 5%-10% of the total Hp protein. Urease decomposes urea to produce ammonia, helping bacteria to colonize in the stomach by neutralizing gastric acid as well as supplying ammonia for bacteria protein synthesis. Therefore, Host tissues of Hp may be injured directly by ammonia or indirectly by the stimulation of urease-induced inflammatory reaction. Blockage of urease gene expression can inhibit the colonization of *Helicobacter pylori* in the host, reduce bacterial protein synthesis, and lower the *Helicobacter pylori*-related inflammatory reaction. Urease B antibody can be detected in all Hp-infected patients especially those with notable symptoms, and the antibody level is, to certain extent, relevant to the seriousness of disease conditions. Oral injection of *Helicobacter pylori* urease or recombinant urease B subunit (rUreB) can protect mice against *Helicobacter pylori* infection and eliminate pre-existing infection (Michetti et al., Gastroenterol. 1994). The activity of urease seems to play an important role in Hp infection, as Hp with loss of activity of urease does not result in infection in animal model. Therefore, an antibody that neutralizes the activity of urease may play a crucial role in resisting against Hp colonization. The above findings indicate that urease antibodies, especially one that is capable of neutralizing the activity of urease, could exert the main role in resisting against Hp infection.

Mucosal immune system is an important part of the body's immune system, mainly including intestinal mucosa-associated lymphoid tissue and bronchus associated lymphoid tissue etc., and it exerts unique action with respect to body defense function. Mesenteric lymph nodes and large quantity of lymphocytes dispersed in lamina propria mucosae and intestinal epithelia constitute immune induction sites and immune effect sites. Through uptaking, processing and extracting antigens, various immunocytes on the surface of gastrointestinal mucosa etc. produce and secrete antigen-specific antibodies (mainly sIgA) which specifically bind with antigen-carrying bacterial or viral vectors to prevent them from colonizing to mucosa surface or invading body, thus exerting certain immunological defense function.

However; the severest defect of mucosal immune system is that it is liable to develop immunological tolerance to antigens. Even with enhanced level of antigen, the level of antigen-specific sIgA produced by the body or mucosa remains very low, and the immune defense ability to the infection of the antigen-carrying microorganisms is dismal.

Heat labile toxin (LT) is a heat-labile enterotoxin produced by enterotoxigenic *Escherichia coli* (ETEC) and capable of inducing severe diarrhea in human and some domestic animals. LT is composed of one A subunit (LTA) and five B subunits (LTB). Spatially five completely identical LTBs form a circular pentamer, and the center of which lies the LTA with its C terminal bound to LTB via noncovalent bonds. The A subunit is composed of two subunits A1 and A2, linked by disulfide bond, wherein A1 is the toxic portion of the toxin whereas A2 binds with the B subunit. All the A and B subunits in cytoplasm exist in the form of precursor carrying signal peptides, and only assemble into intact LT after passing through cell membrane. The B subunit serves to specifically bind with GM1-ganglioside receptor on the surface of eukaryotic cell to make the conformational transition of LT molecule; the A subunit dissociates from the B subunit and enters into cell membrane, followed by disulfide bond degradation and A1 peptide chain activation; and the A1 subunit has the activity of GTP-independent ADP-ribosylation transferase, which destructs the degradation and balance of intracellular cAMP through G protein-mediated ADP-ribosylation reaction and triggers the rise of cAMP level, thus inducing toxin effect.

LT is considered a promising mucosal immune adjuvant in recent years. The research by Rollwagen etc. showed that LT can strengthen mucosal immune response to campylobacteria and accelerate the elimination of the bacteria in the intestinal tract; and furthermore, animals initially immunized with LT and an antigen do not develop immunological tolerance to the antigen even after a long-term observation.

The viewpoint that LT can be used as mucosal immune adjuvant has been generally accepted (Lycke N, et al. Immunology, 1986, 59(2):301-308; Clements J D, et al. Vaccine, 1988, 6(3):269-277; Giuliani M M, et al. J. Exp. Med., 1998, 187(7):1123-1132). Since LT has very strong intestinal toxicity, consequently its B subunit or constructed nontoxic or low toxic LT mutant were mainly used as adjuvant (Yamamoto M, et al. J. Immunol., 1999, 162:7015-7021; Martin M, et al. J. Immunol., 2002, 169(4):1744-1752; Tamura S I, et al. Vaccine, 1994, 12:1238-1240). However, the A subunit of LT, in addition to its ADP-ribosyl enzyme activity, also relates to adjuvant activity (Giuliani M M, et al. J. Exp. Med., 1998). LTA chain stimulates the isotype switching of mucosa-associated B cells and meanwhile LTA participates in the initial phase of mucosal immune response, making type-fixed IgA B cells migrate from production site to distal effect site (De-Hann L, et al. Vaccine, 1996; (4):260-266). De Haan etc. found that LT mutant lack of ADP-ribosyl enzyme activity still possesses adjuvant activity, suggesting that the adjuvant activity of LT is independent of the A1 subunit with ADP-ribosyl enzyme activity while the A2 subunit may contribute to the adjuvant activity of LT. De Haan's experiments also demonstrated that, through immunizing mice via nasal cavity mucosa, the LT mutant without toxic activity still keeps the immune properties of the wild-type toxin The single use of recombinant LTB shows a weaker immunogenicity than that of LT mutant without toxic activity (De Haan L, et al. Infect Immun, 1996), suggesting that the ADP-ribosyl enzyme activity of LTA does not directly relate to the immunity of the toxin. Additionally, LT whole toxin produces high-level systemic IgG and mucosal S-IgA responses while equal amount of LTB merely produces a low-level IgG response. That the immunogenicity of LT is stronger than that of LTB indicates that LTA plays an important role in the immune response of the toxin. Whereas the GTP-dependent ADP-ribosyl transferase activity possessed by the A1 subunit is related to the toxin effect, the adjuvant effect of the LTA is hinted mainly exerted by LTA2 subunit.

LTB has been used as an immunological adjuvant at present. For example, LTB is fused with UreB to form recombinant protein LTB-UreB (Wuchao, Zou quanming etc. *Research on fusion and expression of Helicobacter pylori UreB and Escherichia coli LTB genes. Chinese Journal of Microbiology and Immunology,* 2002, 22(2):175-179), and can be prepared into intramolecular adjuvant vaccine. However, the immunoprotection rate of the recombinant protein has yet to reach the desired level.

Based on above-mentioned, a recombinant Hp subunit intramolecular adjuvant vaccine with enhanced strength and complete protection against *Helicobacter pylori* infection, that can also be conveniently administered, is especially of demand in the field.

DESCRIPTION OF THE INVENTION

One of the objectives of the invention is to provide a recombinant protein used for immunoprophylaxis and treatment of human *Helicobacter pylori* infection, and the recombinant protein can be prepared into recombinant *Helicobacter pylori* vaccine used for immunoprophylaxis of human *Helicobacter pylori* infection.

Another objective of the invention is to provide a method for preparing the mentioned recombinant protein used for immunoprophylaxis and treatment of human *Helicobacter pylori* infection.

A further objective of the invention is to provide a recombinant *Helicobacter pylori* vaccine used for immunoprophylaxis and treatment of human *Helicobacter pylori* infection, which comprises the above mentioned recombinant protein used for immunoprophylaxis and treatment of human *Helicobacter pylori* infection.

Another objective of the invention is to provide a method for preparing the above mentioned recombinant *Helicobacter pylori* vaccine used for immunoprophylaxis and treatment of human *Helicobacter pylori* infection.

In order to realize above objectives, the invention provides a recombinant protein used for prophylaxis and treatment of human *Helicobacter pylori* infection, and the recombinant protein (LTA2B-UreB, LU for short) is obtained by fusion of the A2 subunit and B subunit of the LT of enterotoxigenic *Escherichia coli* and *Helicobacter pylori* urease B subunit. In the recombinant protein, LTA2B is used as an intramolecular mucosal immunological adjuvant and the UreB is used as an immunogen. LTA2B lacks the A1 portion that has ADP-ribosyl enzyme activity of a LT molecule, therefore overcomes the toxic and adverse side effects of a LT adjuvant. Meanwhile, comparing to commonly used adjuvant LTB, LTA2B for the first time adds in the A2 portion of the LT, thereby enhancing its adjuvant activity and immunogenicity.

In one embodiment of the invention, it is demonstrated that the LTA2B-UreB fusion protein has the similar biologic activity, immunogenicity, and reactionogenicity with the full-length UreB, and has the function of enhancing the activity of mucosal adjuvant.

The invention also provides a slow-releasing microsphere-encapsulated oral preparation used for immunoprophylaxis and treatment of human *Helicobacter pylori* infection, wherein the preparation encapsulates the above mentioned recombinant protein used for prophylaxis and treatment of human *Helicobacter pylori* infection.

The invention adopts degradable slow-releasing microspheres (MS) to encapsulate the above-mentioned recombinant fusion protein. Firstly, the slow-releasing microspheres can effectively prevent the antigen from being decomposed and destructed by gastric acid and the enzymes in the digestive tract so as to retain the whole stability and activity of the antigen; secondly, since the MS particle diameter size determines its in-vivo distribution in various organs, manipulation of the preparation process of MS can control the particle diameter within a certain range, thereby purposely directing the particles to targeted organs so as to maximize immunological efficacy. When encapsulating the antigen, the particle diameter of MS and the adhesive action between the antigenic substance and MS can be modified through altering the proportion ratio of the carrier and antigen as well as the biodegradable carrier material, thus achieving the effect of long-lasting and slow release of the antigen.

In a preferred embodiment, said encapsulation substances include alginate, vegetable oil, calcium chloride, and chitosan. In a preferred embodiment, the particle diameter of said microsphere-encapsulated preparation is 3.33 µm.

In a preferred embodiment, said slow-releasing microsphere-encapsulated preparation is at the end developed into freeze-dried preparation for oral immunization, wherein the excipient of the freeze-dried preparation is 8% mannitol, the stabilizing agent is 0.05% EDTA-Na$_2$, and the optimal pH value is 10.0. Oral administration has the following advantages: firstly, the antigenic ingredients of the vaccine directly stimulate gastrointestinal mucosa-associated lymphocytes and produce relevant mucosal immune response through the recognition and the presentation of the intestinal antigen and immune effect, thus achieving the objective of effective prevention of related diseases that would be caused by *Helicobacter pylori* infection; secondly, oral immunization is a painless and noninvasive therapy, and it is convenient, of low cost, and has easy compliance among examinees.

The invention further provides a nucleotide sequence encoding said recombinant protein, wherein the nucleotide sequence is ltA2B-ureB (lu for short) formed by fusion of the coding gene of A2 subunit and the coding gene of B subunit of heat-labile enterotoxin of enterotoxigenic *Escherichia coli*, and the coding gene of urease B subunit of *Helicobacter pylori*.

The invention also provides a recombinant plasmid, wherein said plasmid was formed by linking said nucleotide sequence of claim 8 and plasmid pET-11c.

The present invention further provides a method for preparing the recombinant protein of claim 1, which comprises the following steps:

(1) respectively cloning the encoding nucleotide sequences of urease B subunit UreB of *Helicobacter pylori* and subunit of heat-labile enterotoxin LTA2B of enterotoxigenic *Escherichia coli*, or cloning the encoding nucleotide sequences of the amino acid sequences having above 95% homology to them and also having the activity of their proteins;

(2) linking the nucleotide sequences obtained by cloning in the step (1) by the method of overlapping PCR to form fusion gene ltA2B-ureB;

(3) constructing the fusion gene ltA2B-ureB on a vector, transforming a host, and expressing recombinant protein LTA2B-UreB; and (4) separating and purifying the recombinant protein obtained from the step (3).

In a preferable embodiment, ltA2B-ureB fusion gene is constructed to vector pET-11c, *Escherichia coli* BL21(DE3) is transformed, and recombinant engineered bacteria pET-11c-LU/BL21(DE3) is constructed. The obtained recombinant plasmid comprises at least one encoding nucleotide sequence of the LU amino acid sequence or the amino acid sequence having above 95% homology to it and also having its protein activity.

In a preferred embodiment, recombinant protein LTA2B-UreB is expressed from said recombinant engineered bacteria by fermenting in 80L fermentor.

The invention also provides a method for preparing an oral recombinant *Helicobacter pylori* vaccine, which comprises the following steps:

(1) proportioning the recombinant protein obtained in claim 9 with sodium alginate, vegetable oil, calcium chloride, and chitosan, and preparing into degradable slow-releasing microsphere-encapsulated preparation; and (2) optionally preparing the slow-releasing microsphere-encapsulated preparation into freeze-dried product.

In a preferred embodiment, the obtained recombinant protein is evenly mixed with sodium alginate solution, followed by adding vegetable oil, after emulsification, adding dropwise to calcium chloride solution by reverse titration, and preparing into sodium alginate-encapsulated protein microsphere preparation; the obtained microsphere preparation is then immobilized, followed by washing and centrifugation to collect pellets, and re-suspending; it is added to a chitosan solution for re-encapsulation to obtain protein microspheres double encapsulated by chitosan and sodium alginate; the microsphere suspension is slowly poured into vials with liquid level lower than 1 cm, followed by pre-freezing in an refrigerator at −40□ for 12 h, directly placing in a chilled vacuum drier for drying, slowly raising the temperature to rapidly sublimate water, and taking out the freeze-dried product for testing when a gas pressure indicator shows no gas is being generated.

In an embodiment of the invention, animal experiments of the obtained vaccine are performed to detect safety and immunogenicity of the recombinant *Helicobacter pylori* vaccine.

In another embodiment of the invention, clinical experiments of the vaccine in human body are performed to verify immunological effects of the recombinant *Helicobacter pylori* vaccine.

From what has been mentioned above, the invention uses LTA2B fused from A2 subunit and B subunit of the LT of enterotoxigenic *Escherichia coli* as a mucosal immune intramolecular adjuvant and uses urease B subunit as an immunogen to construct a recombinant *Helicobacter pylori* vaccine which is used conveniently and safely for effective immunoprophylaxis of human *Helicobacter pylori* infection.

To further illustrate the objectives, characteristics, and advantages of the present invention, the following examples in combination with figures are provided.

EXAMPLES

Example 1

Construction of Fusion Gene lu (ltA2B-ureB)

Figure 1:
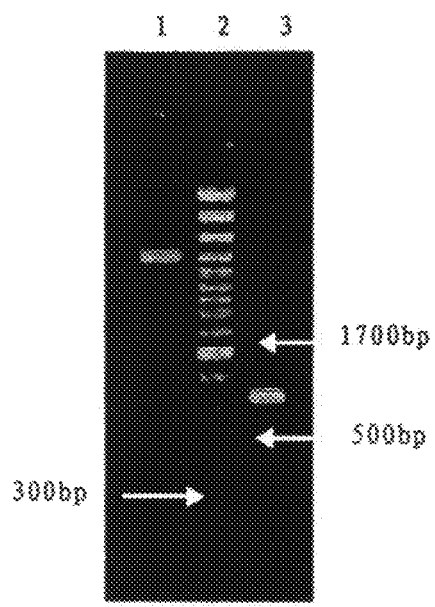
FIG. 1 depicts the agarose gel electrophoresis pattern of lu (ltA2B-ureB) fusion gene obtained by overlap-extension method, wherein lane 1 is the PCR amplification product of ureB gene; lane 2 is nucleic acid (DNA) molecular weight marker; and lane 3 is the PCR amplification product of ltA2B fusion gene.

(1) Cloning of Encoding Genes of *Helicobacter pylori* UreB and Enterotoxigenic *Escherichia coli* LTA2B The genomic DNA of wild-type enterotoxigenic *Escherichia coli* H44815 (purchased from National Institute for the Control of Pharmaceutical and Biological Products) and the genomic DNA of *Helicobacter pylori* NCTC 11637 (purchased from American Type Culture Collection, ATCC) were respectively used as templates; P1 and P2, and P3 and P4 were respectively used to amplifying ureB and ltA2B genes; and the extraction of the bacterial genomes was performed according to conventional method (Yan ziyin, Wang Hailin translated. *Short Protocols in Molecular Biology. Science Press,* 1998, P39). The PCR amplification system was: 10× magnesium ion-free amplification buffer solution 10 μL, MgCl$_2$ (25 mmol/L) 10 μL, dNTPs (2.5 mmol/L each) 8 μL, upstream and downstream primers (P1 and P2 or P3 and P4) respectively 2 μL, the above bacterial genomes 2 μL, Ex-Taq DNA polymerase (3 U/μL) 1 μL, and sterilized water added up to 100 μL.

PCR amplification reaction: pre-denaturation at 94° C. for 5 min, denaturation at 94° C. for 50 s, annealing at 60° C. for 50 s, extension at 72° C. for 50 s, for 35 cycles by a final extension step at 72° C. for 10 minutes. The target fragments were recovered after agarose gel electrophoresis. (The underlined portion was the recognition sequences of corresponding enzymes).

94° for 5 min, denaturation at 94° for 50 s, annealing at 60° for 50 s, extension at 72° for 50 s, for 35 cycles by a final extension step at 72° C. for 10 minutes. The target fragments were recovered after agarose gel electrophoresis. (The underlined portion was the recognition sequences of corresponding enzymes).

(SEQ ID NO: 3)
P1:
<u>cat atg</u> gct cct cag tct att aca gaa cta tgt tc
 NdeI (SEQ ID NO: 4)
P2:
tga tat <u>cgg atc ctg</u> agg gta gtt ttc cat act gat
            BamHI
tgc c (SEQ ID NO: 5)
P3:
tac cct <u>cag gat ccg</u> ata tca atg aaa aag att agc ag
            BamHI (SEQ ID NO: 6)
P4:
<u>cat atg</u> cta gaa aat gct aaa gag ttg tgc caa gc
 NdeI The plasmid DNA of TA cloned and transformed bacteria strain was extracted according to conventional method (J. Sambrook, *Molecular Cloning, Cold Spring Harbor Laboratory Press* 1989 *Polyacrylamide Gel Electrophoresis* 1.21- 1.32), and sequencing of insertion fragments was carried out by dideoxy termination method.

(2) Construction of Fusion Gene ltA2B-ureB

PCR products of ureB and ltA2B were respectively recovered. Overlap extension PCR was performed by using recovered ureB and ltA2B genes as templates and P1 and P4 as primers. PCR amplification system was: 10× magnesium ion-free amplification buffer solution 5 μL, MgCl$_2$(25 mmol/L) 4 μL, dNTPs (25 mmol/L) 4 μL, upstream and downstream primers (P1 and P4) respectively 1 μL, the above ureB and ltA2B genes respectively 2 μL, Ex-Taq DNA polymerase (5 U/μl) 0.5 μL, and sterilized water added up to 50 μL.

Overlap extension PCR amplification reaction: pre-denaturation at 94° C. for 5 min, denaturation at 94° C. for 60 s, annealing at 60° C. for 60 s, extension at 72° C. for 60 s for 35 cycles by a final extension step at 72° C. for 10 minutes, The target fragments were recovered after agarose gel electrophoresis.

The cloning and sequencing of PCR products are the same as previously described.

| Overlap extension PCR reaction system | |
|---|---|
| Recovered ureB DNA fragment | 1 μl |
| Recovered ltA2B DNA fragment | 1 μl |
| P1 (5 pmol/μl) | 2 μl |
| P4 (5 pmol/μl) | 2 μl |
| 10×PCR buffer solution | 10 μl |
| dNTPs (5 mmol/L) | 4 μl |
| Taq plus DNA polymerase (3 U/μl) | 1 μl |
| ddH$_2$O | 79 μl |
| Total volume | 100μ |

Figure 2:
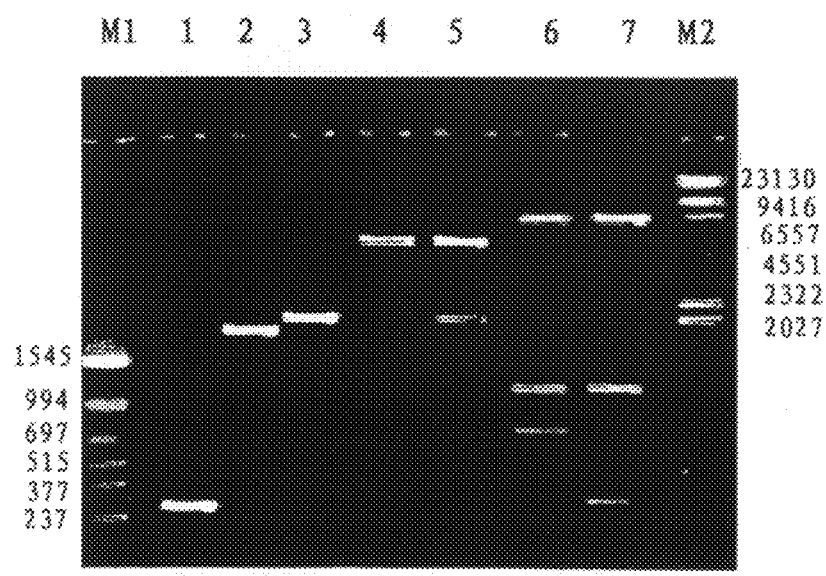
FIG. 2 depicts the enzyme digestion identification of recombinant plasmid pET-11c-lu, wherein lane M1 is PCR Marker; lane 1 is lt A2B PCR product (about 0.4 kb); lane 2 is ureB PCR product (1.7 kb); lane 3 is lu PCR product (about 2.1 kb); lane 4 is pET-11c NdeI digestion (5.7 kb); lane 5 is pET-11c-lu NdeI digestion (5.7 kb+2.0 kb); lane 6 is BamHI enzyme digestion of sense recombinant of pET-11c-lu (6.0 kb+1.0 kb+0.7 kb); lane 7 is BamHI enzyme digestion of antisense recombinant of pET-11c-lu (6.4 kb+1.0 kb+0.3 kb); and lane M2 is λDNA/HindIII Marker.

The reaction system was oscillated and mixed evenly, and 20 μl of paraffin oil was added after centrifugation; followed by pre-denaturation at 94° C. for 10 min, denaturation at 94° C. for 30 s, annealing at 58° C. for 45 s, extension at 72° C. for 1 min, for 35 cycles by a final extension step at 72° C. for 10 minutes 3 μl of reaction product was taken after the reaction was completed; and the PCR amplification product was detected by 1% agarose gel electrophoresis and the target gene fragment ltA2B-ureB was recovered. ltA2B-ureB fusion gene fragment was obtained by using overlap extension PCR technique. 1% agarose gel electrophoresis analysis (see FIG. 1), the fragment size as shown in the pattern was coincident with the anticipated (about 2.1 kb) and it was primarily judged as the target gene fragment and named as ltA2B-ureB as represented by SEQ ID NO:1. The FIG. 2 showed that the size of the fusion gene fragment was coincident with the anticipated, which indicated that the fusion gene was obtained by overlap extension.

Example 2

Construction of Recombinant Engineered Bacteria pET-11c-LU/BL21(DE3)

1 Construction of Recombinant Engineered Bacteria pET-11c-LU/BL21(DE3)

The amplification (PCR) product of lu (ltA2B-ureB) fusion gene was subjected to 1.0% agarose electrophoresis, gel recovery, and purification, followed by ligating with vector pMD-18T (purchased from TaKaRa company), transforming *Escherichia coli* DH5α, extracting plasmids, digesting with NdeI, and identifying by 1.0% agarose gel electrophoresis.

Plasmid DNA was extracted from positive recombinant bacteria of pMD-18-lu/DH5α, then performing NdeI digestion, recovering 2.0 kb lu DNA fragment, ligating with NdeI-digested dephosphorylated pET-11c vector (purchased from America Novagen Co.), transforming *Escherichia coli* DH5α, screening with ampicillin-positive LB plate, selecting suspect colonies for plasmid extraction, identifying positive recombinant by NdeI digestion, and digesting with BamHI for identification of forward and reverse directions. The digestion identification results were showed in FIG. 2. The positive recombinant plasmid DNA generated both 5.7 kb of vector fragment and 2.1 kb of lu gene (the fifth lane) fragment after NdeI digestion; the antisense recombinant produced 6.4 kb+1.0 kb+0.3 kb three fragments (the seventh lane) after BamHI digestion; and the sense recombinant produced 6.0 kb+1.0 kb+0.7 kb three fragments (the sixth lane).

The relevant specific operation steps were shown as follows:

1) A plasmid extraction kit provided by Omega corporation was used to extract plasmid DNA by the recommended method according to the description of the kit.

2) Plasmid DNA was separated by conventional method of agarose gel electrophoresis (1.0% agarose gel, 1×TAE buffer solution, electrophoresis was performed at 120-150 mA for 20-40 min. formulation of 50×TAE storage solution: 2.0 mol/L Tris base, 1.0 mol/L NaAc, and 0.1 mol/L $Na_2EDTA$; and the pH of the solution was regulated to 8.3 by using glacial acetic acid).

3) Digestion identification of plasmid DNA: the reaction mixture includes: 1 mg plasmid DNA; 1 μl 10× buffer solution (see the product description of Shanghai shenggong Co.); 1 μl restriction enzyme Nde I (10u/μl); double distilled water was added up to 10 μl; incubation at 37° C. for 1-2 h after mixing.

4) Recovery and purification of the target DNA from agarose electrophoresis gel:

The target DNA electrophoresis bands were observed under ultraviolet lamp and cut from the agarose gel, and transferred into a 1.5 ml of EP tube.

A DNA-binding buffer solution of the gel recovery kit of Omega corporation was added, then carrying out water bathing at 65° C. to completely dissolve the gel, keeping the solution pH within 5.0-6.0; transferring the dissolved gel solution into a separator tube, centrifuging at 12000 g for 1 min, and discarding the liquid from the collection tube.

A corresponding washing buffer solution was added, then centrifuging at 12000 g for 1 min, and discarding the liquid from the collection tube, washing repeatedly for one time.

Centrifuging at 12000 g for 1 min, followed by transferring the separation tube into another clean 1.5 ml EP tube, adding a certain volume of TE buffer solution, incubating at 65° C. for 10 min, centrifuging at 12000 g for 1 min, taking out a certain amount for electrophoresis, and detecting the recovery and purification effects with a UVP ultraviolet scanner.

5) Ligation reaction (using the ligation kit of Shanghai Shenggong Co.)

The concentrations of the target DNA fragments and vector fragments were determined by using an ultraviolet spectrophotometer; and according to the principle that the mole ratio of the exogenous fragments to the vector was generally 1:(2-10), the ligation reaction system was designed as follows:

Target DNA 1 μl; plasmid vector 1-2 μl; ligation solution 5 μl; $ddH_2O$ 2-3 μl; and total volume 10 μl. Ligation reaction for 12-16 h at 22° C.

6) Preparation of competent bacteria ($CaCl_2$ method)

Dipping a bacterial-preserving liquid freeze-stored at −70° C. by using an aseptic inoculating loop, performing streak inoculation on LB plate by three line method, and culturing at 37° C. for 12-16 h; choosing single colony and inoculating to 2 ml of LB culture fluid, and shake culturing at 37° C. for 12-16 h; transferring inoculating overnight cultured DH5α at 1% ratio to LB culture fluid, shaking culture at 37° C. for 0.2-0.4 h until $OD_{600}$, centrifuging at 8000 g for 5 min, and collecting the bacteria; adding 1 ml pre-chilled 0.1 M $CaCl_2$ to re-suspend pellets, and performing ice water bath for 3 h; centrifuging at 8000 g at 4° C. for 5 min and discarding the supernatant; and adding 100 μl of pre-chilled 0.1 M $CaCl_2$ to suspend pellets, and performing ice water bath for 1 h for subsequent use.

7) Transformation of *Escherichia coli* host cells using ligation product

Taking competent bacteria suspension 100 μl and adding ligation reaction product subjecting to ice water bath for 60 min, water bath at 42° C., heat shock for 100 s, and prompt ice water bath for 1-2 min; adding 100 μl LB culture fluid, shake culturing at 37° C. for 1 h; centrifuging at 8000 g for 10 min, sucking to discard 100 μl of supernatant, mixing pellets, respectively taking 50 μl for smearing onto plate, and culturing at 37° C. overnight in an incubator.

2. Construction and Screening of Engineered Bacteria Highly Expressing Fusion Protein Recombinant expression plasmid containing LU fusion gene was transformed into *Escherichia coli* BL21, and plasmid was extracted, digested, and identified. FIG. 2 is the agarose gel electrophoresis pattern for digestion identification of recombinant expression plasmid pET-11c-LU/BL21 (DE3), wherein lane 5 is NdeI digestion product of recombinant plasmid pET-11c-LU/BL21(DE3); lanes M1 and M2 are molecular weight marker of nucleic acid (DNA); lane 4 is NdeI single enzyme digestion product (5700 bp) of empty vector plasmid. The digestion fragment size was consistent with the experiment design, suggesting the construction of recombinant plasmid was successful. The preparation and transformation of competent bacteria of genetically-engineered *Escherichia coli* BL21, and the extraction and digestion identification of the plasmids of recombinant bacteria were the same as previously described.

Figure 3:
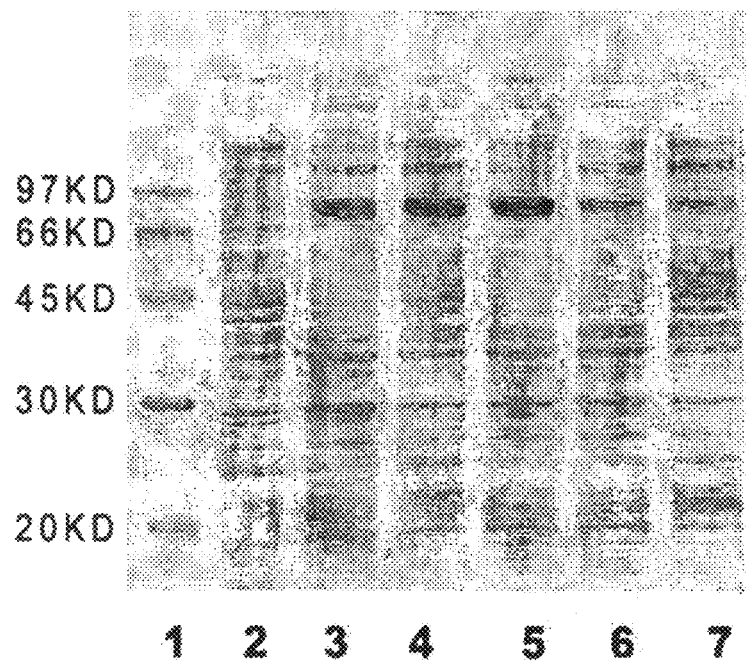
FIG. 3 depicts PAGE electrophoresis pattern of fusion gene lu in recombinant bacteria, wherein lane 1: protein molecular weight marker; lane 2: 1 hour of induction of plasmid-free bacteria; lane 3: five hours of induction of genetic recombinant bacteria; lane 4: four hours of induction of genetic recombinant bacteria; lane 5: three hours of induction of genetic recombinant bacteria; lane 6: two hours of induction of genetic recombinant bacteria; lane 7: one hour of induction of genetic recombinant bacteria. From the result we can see that the genetic engineered bacteria after induction have an additional protein expression band at molecular weight of 72 KDa, which is coincident with the molecular weight of the target protein. The expression ratio of the target protein after five hours of induction is about 26% as shown by UVP image scanning analysis.
Figure 4:
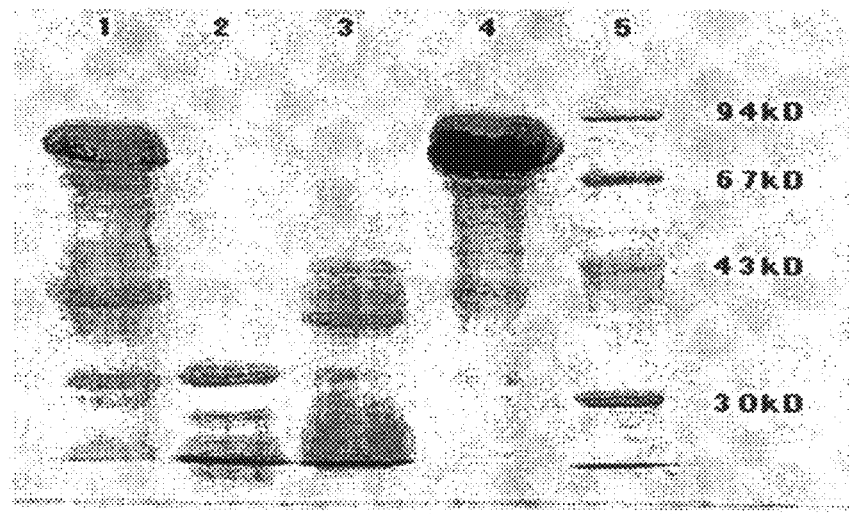
FIG. 4 depicts the PAGE electrophoresis pattern of the purification effect of the target protein LU, wherein lane 1: lysed inclusion body liquid (sample before purification); lane 2 and 3: elution peak sample of impurity proteins; lane 4: elution peak sample of the target protein; and lane 5: protein molecular weight marker. The results show that the purity of the target protein is obviously improved after the step of purification and the purity of the harvested target protein peak analyzed by UVP scanning is greater than 85%.
Figure 5:
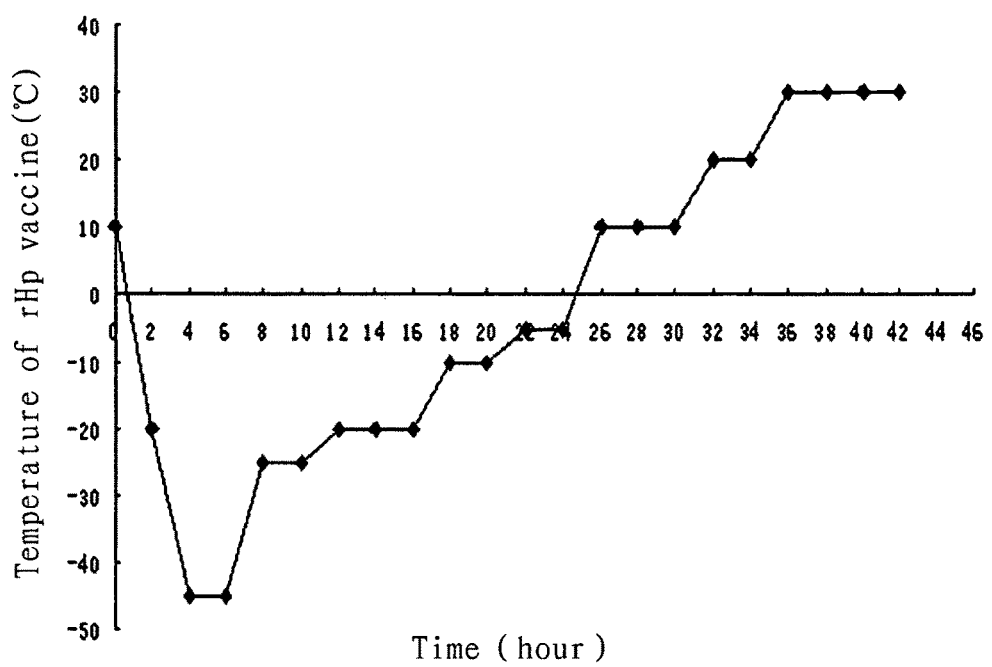
FIG. 5 depicts the freeze drying curve of rHp (recombinant *Helicobacter pylori* vaccine).

Accurately-identified recombinant bacteria were inoculated to 3 ml of kanamycin-containing LB culture fluid, and were shaken at 37° C. overnight. In the next day the overnight-cultured recombinant bacteria were transfer-inoculated at a ratio of 1% to 20 mL of kanamycin-containing LB culture fluid, and were shaken at 37° C. for 2.5 h, induced with IPTG for 5 h, and the expression pattern and expression amount of the fusion protein were detected by SDS-PAGE, and highly-expressed strains were screened, as shown in FIG. 3.

The invention also verified the stability of UreB and LTA2B and that whether they could replace the full-length protein of urease B through experiments. PCR method was adopted to amplify target LTA2B, and UreB and LTA2B fragment genes, followed by constructing to prokaryotic expression vector pET-11c(+), transforming into host bacteria *Escherichia coli* BL21(DE3), and stably expressing LTA2B-UreB fusion protein by inducing with IPTG. Firstly, ELISA and immunoblotting assay verified that recombinant LTA2B-UreB had good immunogenicity and reactionogenicity; secondly, the produced antibody in rabbit immunized with purified LTA2B-UreB neutralized the activity of urease in vitro and showed the similar biological activity to UreB of natural HP; further, the oral immunization of recombinant LTA2B-UreB in BB/c mice was capable of effectively stimulating body to produce Th1/Th2-balanced immune response, which was consistent with recombinant UreB (Wuchao, Zou quanming etc. *Research on fusion and expression of Helicobacter pylori UreB and Escherichia coli LTB genes. Chinese Journal of Microbiology and Immunology*, 2002, 22(2):175-

179); finally, challenge protection test in mice showed that the protection rate of LTA2B-UreB was 91.6% which was significantly higher than the protection rate 68% of the full-length UreB. GM1-ELISA test, indicating that the fused LTA2B-UreB had no ADP ribosyl-enzyme activity while retained the biological property of binding with ganglioside GM1. The challenge protection test in mice also showed that the protection rate of LTA2B-UreB was significantly higher than the protection rate 74.1% of UreB-LTB and the protection rate 78.6% of physically-mixed combination of UreB and LTB. For the first time it has been demonstrated that LTA2B-UreB has the similar biological activity, immunogenicity, and reactionogenicity to that of full-length UreB, and has the function of strengthening the activity of mucosa adjuvant.

Example 3

Fermentation of Recombinant Engineered Bacteria pET-11c-LU/BL21(DE3)

Fermentation process as follows: Germany B.Bron 80L fermentor was adopted; the inoculation ratio of seed strain for fermentation process was 10%; temperature was at 37° C.; and pH was at 7.0. The pH value was kept constant by automatically adding 30% ammonia water; the revolution was initially set at 500 rpm, and the revolution was changed to dissolved oxygen cascade control along with the increase of the bacteria cells and the enhancement of oxygen consumption, that is, a $PO_2$ controller was used as a main controller and a stirring controller was used as servo controller; the dissolved oxygen concentration was controlled by cascade control and negative oxygen bypass control and its final concentration was controlled within 45%-50%; batch materials are not fed when A600 was less than 2 h, followed by flow adding batch materials once every 0.5 h to make the final concentrations of glucose, tryptone, and 8% yeast extract were 0.5%, 0.2%, and 0.2% respectively. After the fourth addition of batch materials and when the glucose concentration reduced to 0.1%, 500 μmol/L IPTG was added to induce for 4 h and bacteria were collected; and flow addition of batch materials was based on the batch culture controlled by dissolved oxygen cascade control during fermentation process.

The culture medium used for fermentation process was modified M9-CAA culture medium, which was based on M9-CAA and supplemented with 0.6% yeast extract liquid and 2 mg/L $ZnCl_2.4H_2O$, 2 mg/L $CoCl_2.4H_2O$, 4 mg/L $FeSO_4.16H_2O$, 5 mg/L $H_3BO_3$, 1.6 mg/L $MnCl_2.4H_2O$, and 4 mg/L $CuSO_4$.

Bacterial suspension was recovered after the fermentation was completed and centrifuged at 8000 g for 15 min. The supernatant was sucked and discarded and bacteria were collected, weighed, and stored by freezing for subsequent use.

Results: the results showed that the yields of the bacteria were all higher than 75 g/L; and the expression amounts of the target proteins were all stabilized at 30% or so, which demonstrated that the mid-scale fermentation process was advanced and had higher levels in both reproducibility and stability.

Example 4

Purification of Recombinant Protein LU (LTA2B-UreB)

1. Extraction of inclusion body: 5000 g of highly-expressed bacteria were suspended in TE buffer solution in a ratio of 1:10(W/V), and then evenly mixed with a cell homogenizer after pre-chilling at 4° C. A high-pressure homogenizer was adopted to break up bacteria cells under a pressurized condition of 40-70 Mpa (totally for 4-6 times). Once finished, a small amount of the bacteria broth was taken, smeared, dyed, to observe the integrity of the cells under a microscope to ensure cells were completely broken up. The bacteria broth was then centrifuged at 500 g for 25 min, after discarding pellets, again centrifuged at 15,000 g for 40 min. Then supernatant was discarded and pellets collected; sequentially washing with washing liquids A and B at a ratio of 1:10(W/V) for 2 times respectively under such washing conditions; stirring at 4° C. for 20 min, centrifuging at 15,000 g for 40 min, and collecting the pellets of inclusion bodies; finally, mixing the inclusion bodies with an inclusion body lysing liquid at a ratio of 1:10(W/V), stirring at 4° C. for 3 h, centrifuging at 15,000 g for −45° C. min, and taking the supernatant as the raw material for next step purification.

Buffer solution used for inclusion body extraction: 1) TE buffer solution: 20 mmol/L Tris, 5 mmol/L EDTA, pH 8.0; 2) inclusion body washing solution A: 5 mmol/L EDTA, 20 mmol/L Tris, 1% Triton X-100, pH 8.0; 3) inclusion body washing solution B: 20 mmol/L Tris, 2 mol/L Urea, pH 8.0; 4) inclusion body lysing liquid: 1 mmol/L EDTA, 20 mmol/L Tris, 8 mol/L urea (pH 8.0).

2. Chromatography purification: the purification step was determined as Q Sepharose HP anion exchange column and Sephadex G-25 column chromatography purification, and mid-scale purification was performed by using XK50/30 column on an ÄKTA explorer[100] system. Since ÄKTA explorer[100] system has the characteristics of accurate automation, two sets of ÄKTA explorer[100] systems were adopted to perform continuous automatic chromatography operation through programming and the mid-scale yield of each batch of rHp vaccine can reach 40 g. The target protein was purified by using 20 mmol/L Tris and 5 mmol/L EDTA under pH of 8.0 and NaCl gradient elution was adopted.

3. Although the purity of the recombinant protein purified by Q Sepharose High Performance chromatography reached above 80%, large amount of salt and urea existed, therefore a method of gel-filtration chromatography was adopted for desalting and removing urea according to differences in molecular weight by using conventional molecular sieve filler Sephadex G-25 medium.

4. The purified target protein was subjected to SDS-PAGE to determine its purity. The purity and yield of the finally-obtained target protein were higher than 80% and 79%, respectively.

5. Protein concentration determination by Lowry method

Wherein, the cell-breaking rate of the high-pressure cell-breaking technique used in production of step 1 or mid-scale purification was greater than 98%, and inclusion body pellets were obtained by differential centrifugation.

The affinity chromatography purification filler in step 2 was selected from Chelating Sepharose Fast Flow.

The anion purification filler in step 3 was selected from Q Sepharose HP, Q Sepharose FF, and Q Sepharose XL.

Example 5

Preparation of Oral Recombinant HP Vaccine

1. Preparation of Recombinant LU Protein Microspheres

The recombinant protein prepared in example 4 was evenly mixed with 2% sodium alginate solution under room temperature, followed by adding a vegetable oil, wherein the ratio of the vegetable oil to sodium alginate AGS emulsion was 2:8, emulsifying at 8000 r/min for 10 min, adding dropwise to $CaCl_2$ solution, stirring at 800 r/min for 30 min to form an O/W emulsion, centrifuging to collect pellets, washing, and resuspending; adding the suspension to 1% concentration of chitosan solution, stirring at 800 rpm for 30 min to complete re-encapsulation to give prepared chitosan-sodium alginate double encapsulated recombinant LU protein microspheres, centrifuging and washing for three times, and collecting.

The above microsphere suspension was slowly poured into a glass plate in a liquid level height lower than 1 cm, then pre-freezing in a refrigerator at −40° C. for 12 h, directly placing in a pre-chilled vacuum drying machine for drying, slowly raising the temperature to rapidly sublimate water, and taking out the freeze-dried product for testing when the gas pressure indicator shows that there was no gas being generated.

Respectively taking trace amounts of centrifuged and washed MS, freeze-dried powder, and re-dissolved freeze-dried powder, smearing them onto glass slides, observing under an optical microscope the morphologic change of the microspheres before and after freeze-drying: under the optical microscope we saw that the sizes and shapes of the microspheres after centrifugation and washing were regular, the microspheres after freeze-drying were in irregular distribution including many irregular shapes such as rod shape, spindle shape, and oblate shape, while the number and shapes of the microspheres re-dissolved with equal amount of distilled water substantially restored to original characteristics before freeze-drying. The prepared MS have plump surface, homogenous size, and an average particle diameter of 3.33 μm.

2. Freeze-Drying of Recombinant LU Protein Microsphere Solution

The highly-purified recombinant LU protein was properly diluted, prepared, and loaded into freeze drying vials for freeze drying. A stable and mature rHp vaccine freeze drying curve was obtained through studies: the pre-freeze temperature of the product was 45° C. and the pre-freeze time was 4 h; the temperature of the first sublimation was 20° C. and sublimation time was 30 h; the temperature of the second sublimation was 30° C. and sublimation time was 8 h; the entire duration of the whole freeze drying process was 42 h; water contents were all less than 3% which met detection requirements with respect to water content of freeze-dried products as recorded in the second part of [[Pharmacopoeia of The People's Republic of China ]] (2000 edition).

Through systemic research on the freeze-drying pilot process, the excipient of the freeze-dried rHp vaccine preparation was determined as 8% mannitol, the stabilizing agent was 0.05% $EDTA\text{-}Na_2$, and optimal pH value was 10.0; and mature parameters such as freeze-drying curve were obtained. Over 20 batches of repeated verifications manifested that the freeze-drying pilot process was stable in performance and met the requirements for scale production. Forty grams of vaccine protein can be dispensed into about 2600 vials calculated as 15 mg of packaged amount of each freeze-drying vial. The adopted 5 $m^2$ of freeze-drying machine can freeze dry and prepare about 5000 freeze drying vials with diameter of 32 mm in one time, meeting the requirements for freeze drying of large quantity of products.

The invention has further revealed the influence of artificial gastric fluid on the stability of the rHp vaccine. Since the rHp vaccine is a freeze-dried preparation for oral immunization, during the process of reaching target organs through digestive tract inevitably it has to pass through the acidic pH environment in stomach. A protein substance in nature, the rHp vaccine is liable to be denatured by acid action or degraded by enzymes, thus reducing its immunological activity. Research discovered that the antigen reactivity of the rHp vaccine protein was obviously reduced and protein degradation was marked in an artificial gastric fluid with pH values of 1 and 2, while a higher antigen reactivity and protein stability were retained in an environment with pH of 3-7. The research result indicated that, during the application process, a method of neutralizing gastric acid can be adopted to properly raise the pH value of the environment in stomach, so as to retain the biological activity of the rHp vaccine protein and thus acquiring favorable immune effects. With respect to the dosage form for an oral recombinant vaccine, an advanced and practical process for poly-microencapsulated preparation resistant to gastric acid and pepsin was established, overcoming the destruction by gastric acid and pepsin. As a result, the efficacy and the stability of the vaccine were improved.

Example 6

Animal Experiments of Oral Recombinant HP Vaccine

1. Safety Evaluation in Animals $LD_{50}$ was not calculated since no abnormal reaction, toxic symptom and death were observed in any tested mice in the $LD_{50}$ group, meanwhile the maximum tolerated dose (MTD) of the rHp vaccine for oral intake was greater than 150 mg/kg (equal to 600 times of the recommended normal dose for human body) as detected through maximum tolerated dose test. During the period of observation after intraperitoneal injection of three batches of rHp vaccine, all of the three batches of guinea pigs survived without abnormal toxic reaction and all the guinea pigs gained weight normally up to the seventh day. The following experiments were respectively carried out and the results indicated that the rHp vaccine had a good safety profile.

2. Research on Immunogenicity

The immunogenicity of the rHp vaccine was observed by respectively using rabbit, BALB/c mice, and rhesus monkey.

(1). Research on Immunogenicity of RHP Vaccine by Immunization of Rabbits

Double immunodiffusion test and ELISA detection were performed after immunizing rabbits with the rHp vaccine, and the results showed that the vaccine induced rabbits to produce high titer of antiserum against UreB, which demonstrated that the rHp vaccine protein had good immunogenicity.

(2). Research on Immunogenicity of the rHp Vaccine by Immunization of BALB/c Mice Each group of BALB/c mice was simultaneously fed with a prepared Hp bacterial suspension at the 10th day after the last immunization. All of the experimental animals were subjected to fasting diet and water 24 h in advance, and each BALB/c mouse was fed with 0.3 ml of bacterial suspension of about $10^8$ cfu/ml (colony forming units per mL) respectively in the morning and the afternoon with an interval time of 6 h, and was provided with diet and water 2 h after the last feeding. All of the experimental animals were killed 4 weeks after the challenge and samples were collected, wherein fasting diet and water was performed 24 h before the sacrifice; followed by dissecting the BALB/c mice, taking out the stomach, splitting along the greater curvature of the stomach, slightly rinsing out the residuals from the stomach with normal saline, smearing half of the gastric mucosa tissue onto a Hp culture medium, performing three-line streak inoculation, and carrying out microaerophilic culture. The colonization of Hp in mice after immunization was shown in table 1.

TABLE 1

Challenge immunoprotection effects on mice after oral immunization of fusion protein

| group | | Survival number after challenge | Non-infection number | Protection rate (%) |
|---|---|---|---|---|
| 1 | PBS group (phosphate buffer solution, pH 7.0) | 28 | 27 | — |
| 2 | UreB group | 30 | 20 | 66.7 |
| 3 | UreB + LTB group | 29 | 19 | 65.5 |
| 4 | UreB + LTA2B group | 27 | 21 | 71.3 |
| 5 | UreB – LTB group | 30 | 24 | 72.8 |
| 6 | LTA2B – UreB group | 29 | 27 | 91.6 |

"UreB – LTB" and "LTA2B – UreB" represent fusion protein, and "UreB + LTB" and "UreB + LTA2B" represent the physical mixing of two kinds of recombinant proteins.

The results denoted that the protection rate of the mice in LU-immunized group (the sixth group) reaches above 90%.

Conclusion: the immunization of the fusion vaccine antigen LU to mice can produce effective protection against whole-cell Hp challenge as compared with non-immunized group.

BALB/c mice confirmed with Hp infection were immunized by intramuscular injection of, respectively, LU fusion protein, in vitro mixture of the two subunits, and controls, all mixed with equal volume of aluminum adjuvant. Injections were made at a dose of 100 µg (100 uL) per mouse at the 0th, the 2th, and the 4th week respectively. Mice were then killed 4 weeks after the last immunization and samples were collected; and the bacteria-carrying status of the mice after treatment was observed through different experimental methods.

TABLE 2

Observation of Hp-infected mice treated with multi-subunit protein vaccine

| Group | Number of post-treatment mice without detected Hp | Number of post-treatment mice with greatly-reduced number of colonized Hp |
|---|---|---|
| LU treatment group (30 mice) | 21 | 9 |
| Two subunit mixing group (30 mice) | 23 | 7 |
| Control group (30 mice) | 0 | 1 |

The p value was lower than 0.001 as shown by the statistical analysis of the two group results, which illustrated that the immunotherapy on infected mice with the vaccine antigen LU or two in-vitro-mixed subunits effectively reduced the bacteria-carrying number in mice or eliminated the infection of the mice. The multi-subunit vaccine antigen including fusion antigen LU had certain therapeutic effects on Hp infection.

3. Experimental Research on Oral Immunization of the RHP Vaccine in Rhesus Monkey The research discovered that the levels of both anti-UreB IgG antibody in serum and sIgA antibody in saliva significantly rose after rhesus monkeys were subjected to oral immunization of the rHp vaccine, and maintain to the 15th week after immunization, which demonstrated that this vaccine can induce rhesus monkey to produce significant systemic immune response and mucosal immune response.

In order to investigate the relationship between the vaccine dose and the immune response level, three different doses were adopted for oral immunization; and the results showed that the induced systemic and mucosal immune response levels in both groups with doses of 0.5 and 2.0 mg/kg were significantly higher than that of the group with a dose of 0.2 mg/kg. No obvious difference was seen between the two groups with the higher doses, suggesting that the optimal dose of the vaccine for oral immunization of rhesus monkey was 0.5 mg per kg of body weight.

The above animal experiments in rabbits, BALB/c mice, and rhesus monkeys have confirmed that the rHp vaccine can effectively induce the mucosal immune response of the bodies and has favorable immunogenicity.

Example 7

The Effect of Oral Recombinant HP Vaccine in Human

In order to demonstrate the therapeutic effects of the invention, clinical studies were performed in the invention. The clinical research data of the invention were shown as follows:
1. Selection criteria:
  (1) Voluntary participation.
  (2) Healthy, determined through consultation of illness history, physical examination, and clinical examination.
  (3) No recent *Helicobacter pylori* infection history.
  (4) No inoculation history of similar vaccines.
  (5) No contraindication for vaccine inoculation.
2. Judgment of therapeutic effects and safety
  (1) Judgment of safety
  30 min of real-time observation was carried out after the subject orally taking the vaccine, and systemic (body temperature) and local (gastrointestinal tract) reactions and other occurrences of abnormal reactions (including fever, abnormal appearances and frequency of stool, diarrhea, and vomiting etc.) were specifically observed at 6 h, 24 h, 48 h, and 72 h after orally taking the vaccine.
  1) Systemic (body temperature) reaction:
  No reaction: body temperature was 37° C. or lower;
  Light reaction: body temperature was in the range of 37.1-37.5° C.;
  Moderate reaction: body temperature was in the range of 37.6-38.5° C.;
  Severe reaction: body temperature was 38.6° C. or above;
  2) Local (gastrointestinal tract) reaction:
  No reaction: no gastrointestinal tract reaction;
  Light reaction: minor gastrointestinal symptoms which were eliminated after common treatment;
  Moderate and severe reactions: required repeated treatment or hospitalization treatment;
  (2) Research on immunogenicity
  The immunogenicity was evaluated according to the antibody status 14 days after the whole-course immunization and the increase and decrease of the antibody were observed 60 days after the whole-course immunization. The positive conversion was defined when the serum-specific IgG was lower than 1:100 before immunization while equal to or higher than 1:100 after immunization; and the positive conversions of serum-specific total Ig and saliva-specific sIgA antibody were defined when their titer ratios before immunization to that of after immunization was equal to or higher than 4 times.
  3. Research Method
  The research was carried out in two stages. The clinical phase I study was non-comparative research, in which 30 healthy children orally took the oral recombinant *Helicobacter pylori* vaccine according to an immunization procedure in a dose of 45 mg every time, and systemic (body temperature) and local (gastrointestinal tract) reactions were observed after oral administration. Clinical phase II study was further carried out if no severe abnormal reaction was observed. The clinical phase II study included random research, double blind research, and comparative research. The research was divided into four groups (see table 4). Immunization procedure: oral immunization was performed three times, once every two weeks, that is, at the 0th, 14th, and 28th day respectively.

4. Research Subjects

Basic information and clinical reaction of subjects for clinical phase I study of oral recombinant *Helicobacter pylori* vaccine were specified as tables 3-5

TABLE 3

Basic information of subjects for clinical phase I study

| Age (year) | Male (number of persons) | Female (number of persons) | Total |
|---|---|---|---|
| 10 | 0 | 1 | 1 |
| 11 | 6 | 6 | 12 |
| 12 | 6 | 7 | 13 |
| 13 | 4 | 0 | 4 |
| Total | 16 | 14 | 30 |

TABLE 4

Basic information of subjects for clinical phase II study

| Group | Number of subjects | Gender composition | | Average age (year) |
|---|---|---|---|---|
| | | Male | Female | |
| placebo | 151 | 77 | 74 | 10.1 |
| 15 mg/per time | 148 | 69 | 79 | 10.3 |
| 30 mg/per time | 171 | 82 | 89 | 10.4 |
| 45 mg/per time | 153 | 74 | 79 | 10.8 |
| Total | 623 | 317 | 306 | 10.2 |

5. Results
1. The Safety of the Vaccine

In the clinical phase I study, 30 subjects received the immunization of the oral recombinant *Helicobacter pylori* vaccine in a dose of 45 mg/per time. No instant reaction, systemic or local reaction, delayed reaction and other abnormal reaction, complication, or any clinically-significant disorders or events was observed in any of the 30 subjects during three-time whole-course immunization (Tables 5 and 6), which indicated that the dose of 45 mg/per time of oral recombinant *Helicobacter pylori* vaccine was safe to human body. According to the results of the clinical phase I study, clinical phase II study of the vaccine was carried out so as to enlarge the population for research on its safety and emphasize on the research of its immunization effects.

TABLE 5

Gastrointestinal reaction in subjects for clinical phase I study of oral recombinant *Helicobacter pylori* vaccine

| Vaccine intake time | Number of observed persons | No reaction No need of treatment | | Light reaction Common treatment | | Moderate and severe reactions repeated treatment and hospitalization treatment | |
|---|---|---|---|---|---|---|---|
| | | number of persons | % | number of persons | % | number of persons | % |
| The first time | 30 | 30 | 100.00 | 0 | 0.00 | 0 | 0.00 |
| The second time | 30 | 30 | 100.00 | 0 | 0.00 | 0 | 0.00 |
| The third time | 30 | 30 | 100.00 | 0 | 0.00 | 0 | 0.00 |

TABLE 6

Systemic reaction in subjects for clinical phase I study of oral recombinant *Helicobacter pylori* vaccine

| Vaccine intake time | Number of observed persons | No reaction (<37.0) | | Light reaction (37.1-37.5) | | Moderate reaction (37.6-38.5) | | Severe reaction (>=38.6) | |
|---|---|---|---|---|---|---|---|---|---|
| | | number of persons | % | number of persons | % | number of persons | % | number of persons | % |
| The first time | 30 | 30 | 100 | 0 | 0.00 | 0 | 0.00 | 0 | 0.00 |

TABLE 6-continued

Systemic reaction in subjects for clinical phase I study of oral recombinant *Helicobacter pylori* vaccine

| Vaccine intake time | Number of observed persons | No reaction (<37.0) | | Light reaction (37.1-37.5) | | Moderate reaction (37.6-38.5) | | Severe reaction (>=38.6) | |
|---|---|---|---|---|---|---|---|---|---|
| | | number of persons | % | number of persons | % | number of persons | % | number of persons | % |
| The second time | 30 | 30 | 100 | 0 | 0.00 | 0 | 0.00 | 0 | 0.00 |
| The third time | 30 | 30 | 100 | 0 | 0.00 | 0 | 0.00 | 0 | 0.00 |

2. Immunogenicity of the Vaccine

The results of the clinical phase II study showed that: all the doses of 15 mg/per time, 30 mg/per time and 45 mg/per time of oral recombinant *Helicobacter pylori* vaccine can stimulate human body to produce favorable serum-specific IgG antibody, serum-specific total Ig antibody, and saliva-specific sIgA antibody responses, and the antibody responses lasted for long duration time and still located at a high level (Table 7-9) two months after the whole-course immunization.

TABLE 7

Positive conversion of serum-specific IgG antibody in subjects for clinical phase II study of oral recombinant *Helicobacter pylori* vaccine

| Group | number of detection samples | 14 days after whole-course immunization | | 60 days after whole-course immunization | |
|---|---|---|---|---|---|
| | | positive conversion number | positive conversion rate (%) | positive conversion number | positive conversion rate (%) |
| placebo | 80 | 4 | 5.0 | 3 | 3.8 |
| 15 mg/per time | 90 | 84 | 93.3 | 86 | 95.6 |
| 30 mg/per time | 90 | 87 | 96.7 | 88 | 97.8 |
| 45 mg/per time | 91 | 84 | 92.3 | 84 | 92.3 |

TABLE 8

Serum-specific IgG antibody level in subjects for clinical phase II study of oral recombinant *Helicobacter pylori* vaccine

| Group | number of detection samples | prior to immunization GMT (1:) | 14 days after whole-course immunization GMT (1:) | 60 days after whole-course immunization GMT (1:) |
|---|---|---|---|---|
| placebo | 101 | 50 | 54 | 54 |
| 15 mg/per time | 116 | 50 | 844 | 1140 |
| 30 mg/per time | 124 | 50 | 1097 | 1251 |
| 45 mg/per time | 114 | 50 | 619 | 859 |

GMT: geometric mean titer

TABLE 9

Saliva-specific sIgA antibody level in subjects for clinical phase II study of oral recombinant *Helicobacter pylori* vaccine

| Group | number of detection samples | prior to immunization GMT (1:) | 14 days after whole-course immunization GMT (1:) | 60 days after whole-course immunization GMT (1:) |
|---|---|---|---|---|
| placebo | 101 | 2.74 | 3.35 | 3.32 |
| 15 mg/per time | 116 | 2.56 | 21.83 | 24.16 |
| 30 mg/per time | 124 | 2.25 | 25.30 | 27.52 |
| 45 mg/per time | 114 | 2.41 | 20.91 | 21.95 |

GMT: geometric mean titer

The invention claimed is:

1. A recombinant protein, wherein said recombinant protein is formed by fusion of an A2 subunit and a B subunit of heat-labile enterotoxin of enterotoxigenic *Escherichia coli* and a urease B subunit of *Helicobacter pylori*, wherein the amino acid sequence of the recombinant protein is presented in SEQ ID NO:2.

2. A slow-release microsphere-encapsulated oral preparation, wherein said preparation encapsulates the recombinant protein of claim 1.

3. The microsphere-encapsulated oral preparation of claim 2, wherein said encapsulation substances include sodium alginate, vegetable oil, calcium chloride, and chitosan.

4. The microsphere-encapsulated oral preparation of claim 2 or 3, wherein the particle diameter of said microsphere-encapsulated preparation is 3.33 μm.

5. The microsphere-encapsulated oral preparation of claim 2 or 3, wherein said encapsulated preparation is a freeze-dried preparation.

6. The freeze-dried preparation of claim 5, wherein the excipient of the freeze-dried preparation is 8% mannitol, stabilizing agent is 0.05% EDTA-$Na_2$, and the optimal pH value is 10.0.

7. A nucleotide sequence encoding the recombinant protein of claim 1, wherein said nucleotide sequence is ltA2B-ureB formed by fusion of the coding gene of an A2 subunit and the coding gene of a B subunit of heat-labile enterotoxin of enterotoxigenic *Escherichia coli*, and the coding gene of a urease B subunit of *Helicobacter pylori*, wherein the nucleotide sequence is presented in SEQ ID NO: 1.

8. A recombinant plasmid, wherein said plasmid is formed by ligation of the nucleotide sequence of claim 7 and the plasmid pET-11c.

9. A method for preparing a recombinant protein wherein said recombinant protein is formed by fusion of an A2 subunit and a B subunit of heat-labile enterotoxin of enterotoxigenic *Escherichia coli* and urease B subunit of *Helicobacter pylori*, wherein said method comprises the following steps:

1) respectively cloning the coding nucleotide sequences of urease B subunit UreB or *Helicobacter pylori* and subunit of heat-labile enterotoxin LTA2B of enterotoxigenic *Escherichia coli*, wherein the amino acid sequence of the recombinant protein is presented in SEQ ID NO: 2;
2) ligating the nucleotide sequences obtained by cloning in the step 1) by the method of overlapping PCR to form fusion gene ltA2B-ureB;
3) constructing the fusion gene ltA2B-ureB on a vector, transforming a host, and expressing recombinant protein LTA2B-UreB;
4) separating and purifying the recombinant protein obtained from step 3).

10. A method for preparing an oral recombinant *Helicobacter pylori* vaccine, which comprises the follow steps:

(1) proportioning the recombinant protein obtained in claim 9 with sodium alginate, vegetable oil, calcium chloride, and chitosan, and preparing into a degradable slow-releasing microsphere-encapsulated preparation; and
(2) optionally preparing the slow-releasing microsphere-encapsulated preparation into a freeze-dried product.

* * * * *